(12) United States Patent
Wender et al.

(10) Patent No.: US 9,016,120 B2
(45) Date of Patent: Apr. 28, 2015

(54) MICRONAIRE MEASUREMENT

(75) Inventors: James T. Wender, Seymour, TN (US);
Preston S. Baxter, Friendsville, TN
(US); Hossein M. Ghorashi, Knoxville,
TN (US)

(73) Assignee: Uster Technologies AG, Uster (CH)

( * ) Notice: Subject to any disclaimer, the term of this patent is extended or adjusted under 35 U.S.C. 154(b) by 887 days.

(21) Appl. No.: 12/617,240

(22) Filed: Nov. 12, 2009

(65) Prior Publication Data
US 2010/0050763 A1    Mar. 4, 2010

Related U.S. Application Data (62) Division of application No. 11/692,826, filed on Mar. 28, 2007, now abandoned.

(51) Int. Cl.
*G01L 5/04*    (2006.01)
*G01N 33/36*    (2006.01)
*G01N 15/08*    (2006.01)

(52) U.S. Cl.
CPC .......... *G01N 33/362* (2013.01); *G01N 15/0826* (2013.01)

(58) Field of Classification Search
USPC ........................................................... 73/159
See application file for complete search history.

(56) References Cited

U.S. PATENT DOCUMENTS

| 2,392,636 | A | * | 1/1946 | Boehler | 73/38 |
| 3,958,734 | A | * | 5/1976 | Fink et al. | 226/1 |
| 4,179,416 | A | * | 12/1979 | Smith | 524/36 |
| 5,001,975 | A | * | 3/1991 | Finden | 100/38 |
| 5,359,880 | A |   | 11/1994 | Elam et al. | |
| 6,098,454 | A | * | 8/2000 | Ghorashi et al. | 73/160 |
| 6,314,806 | B1 | * | 11/2001 | Ghorashi et al. | 73/160 |
| 6,532,798 | B1 | * | 3/2003 | Shofner et al. | 73/38 |

* cited by examiner

*Primary Examiner* — Laura Martin
*Assistant Examiner* — Alex Devito
(74) *Attorney, Agent, or Firm* — Luedeka Neely Group, P.C.; Rick Barnes (57) ABSTRACT

A method of determining a testing volume for a micronaire measurement by containing a fiber sample within a micronaire chamber having a length and at least one movable end wall. A flow is initiated along the length of the micronaire chamber. The fiber sample is compressed within the micronaire chamber by advancing the movable end wall, and the advancement of the movable end wall is stopped when at least one property of the flow attains a set point. The position of the movable end wall defines the testing volume. In this manner, there is provided a convenient method of setting a testing volume and acquiring the information needed to take a micronaire measurement.

3 Claims, 7 Drawing Sheets

MICRONAIRE MEASUREMENT

This application is a divisional application of and claims all rights and priority on prior pending US patent application Ser. No. 11/692,826 filed 2007, Mar. 28. This invention relates to the field of fiber property measurement. More particularly, this invention relates to micronaire measurement of fibers.

FIELD

Background

Micronaire readings are derived from Koxeny's equation, which provides an approximation for the permeability of powders having a negligible number of blind pores. This equation characterizes the relationship of air flow resistance over a surface with a known mass in a known volume, as in:

$$M = (RM)^x$$

when:

$$RM = \left[\frac{(HMC - LMC)}{(LMP - HMP)}\right][LMC + (LMP - P)]$$

and:

$$X = 1 + [(W - 10)100][0.00125 - |3.5 - RM|0.00015]$$

where, over a sample weight range of about eight grams to about twelve grams:
M=Corrected micronaire value
RM=Raw micronaire value
HMC=High calibration cotton value
LMC=Low calibration cotton value
LMP=Pressure of low calibration cotton value
HMP=Pressure of high calibration cotton value
P=Pressure of cotton under test
W=Weight of cotton under test, grams Even though there are certain properties of the fiber sample, cotton for example, that must be known or derived in order to produce a micronaire value, these properties can be determined in a variety of different ways—some ways easier or more convenient than others. Likewise, the method by which the micronaire readings are taken can also vary in efficiency, speed, or convenience of operation.

What is needed, therefore, is a system for measuring micronaire that provides benefits, such as those mentioned above, at least in part.

SUMMARY

The above and other needs are met by a method of determining a testing volume for a micronaire measurement by containing a fiber sample within a micronaire chamber having a length and at least one movable end wall. A flow is initiated along the length of the micronaire chamber. The fiber sample is compressed within the micronaire chamber by advancing the movable end wall, and the advancement of the movable end wall is stopped when at least one property of the flow attains a set point. The position of the movable end wall defines the testing volume.

In this manner, there is provided a convenient method of setting a testing volume and acquiring the information needed to take a micronaire measurement.

In various embodiments, the at least one property of the flow is pressure or volumetric flow rate. The movable end wall is advanced with a stepper motor in one embodiment. The flow is preferably a flow of air. Preferably, the at least one property of the flow and the testing volume are used to calculate the micronaire measurement.

According to another aspect of the invention there is described a method of preparing a fiber sample for a micronaire measurement by forming the fiber sample into a plug having a cross-sectional shape and size that are substantially similar to a cross-sectional shape and size of a micronaire chamber in which the micronaire measurement is to be taken, before inserting the plug into the micronaire chamber.

According to another aspect of the invention there is described a method of preparing a fiber sample for a micronaire measurement by placing an amount of unformed fiber as a fiber sample in a fiber sample loader, and bringing together forming surfaces of the fiber sample loader to form the fiber sample into an elongate plug having a cross-sectional shape and size that are substantially similar to a cross-sectional shape and size of a micronaire chamber in which the micronaire measurement is to be taken, before inserting the plug into the micronaire chamber.

According to another aspect of the invention there is described a method of preparing a fiber sample for a micronaire measurement by placing an amount of unformed fiber as a fiber sample in a fiber sample loader. A first lateral forming surface of the fiber sample loader is brought toward a second lateral forming surface of the fiber sample loader and the fiber sample is formed between the first lateral forming surface and the second lateral forming surface to form three sides of the fiber sample. A vertical forming surface of the fiber sample loader is brought down between the first lateral forming surface and the second lateral forming surface and onto the fiber sample to form a fourth side of the fiber sample, thereby forming the fiber sample into an elongate plug having a cross-sectional shape and size that are substantially similar to a cross-sectional shape and size of a micronaire chamber in which the micronaire measurement is to be taken. The plug is inserted into the micronaire chamber with a plunger having a cross-sectional shape and size that are substantially similar to the cross-sectional shape and size of a micronaire chamber in which the micronaire measurement is to be taken.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Sample Loading and Unloading

Figure 1:
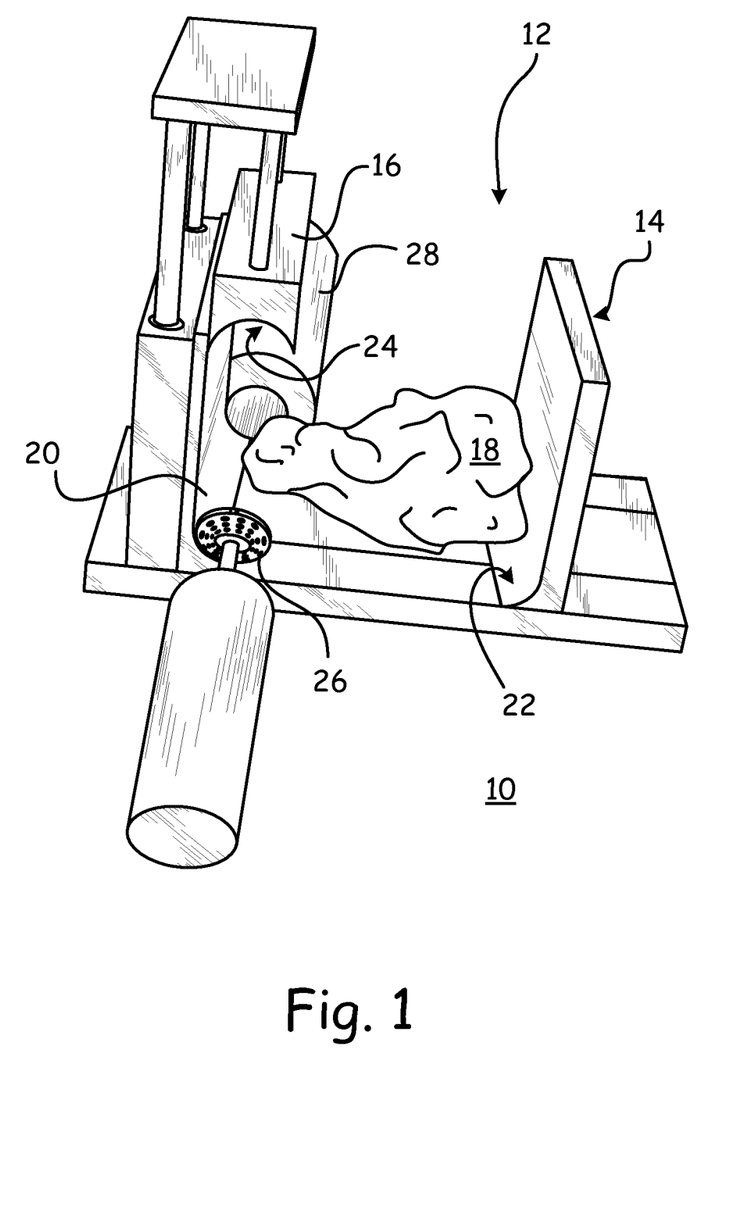
FIG. 1 depicts a micronaire measurement system according to a preferred embodiment of the present invention, with the loader in the sample reception position.

With reference now to FIG. 1, there is depicted a micronaire measurement system 10 according to a preferred embodiment of the present invention. As depicted in FIG. 1, the sample loading mechanism 12 is in the sample reception position, with the lateral plug formation member 14 and the vertical plug formation member 16 extended. With the loader 12 in this position, the loader 12 is adapted to receive the fiber sample 18, on which micronaire measurements are to be made. The fiber sample 18 may be any one or blend of more than one fiber types, but in the preferred embodiment the fiber sample 18 is cotton fiber.

The various elements of the loader 12 are preferably adapted so as to form the fiber sample 18 into a plug 18 that is substantially the same cross-sectional shape as the micronaire chamber 28 into which the plug 18 will be loaded for measurement of the micronaire readings. For example, in the depicted embodiment, the micronaire chamber 28 has a generally circular cross-sectional shape, and thus the loader 12 preferably forms the fiber sample 18 into a plug 18 having a generally circular cross-sectional shape.

To accomplish this, an interior lateral wall 20 of the loader 12 has a rounded bottom corner, to approximate the interior of the micronaire chamber 28 at that equivalent location. Similarly, the exterior lateral wall 22 of the loader 12 also has a rounded bottom corner, again to approximate the interior of the micronaire chamber 28 at that equivalent location. It is appreciated that if the micronaire chamber 28 has a different cross-sectional shape, the elements described would preferably have different shapes than those described herein, which different shapes are again selected so as to approximate the equivalent locations of the micronaire chamber 28. Thus, the desired function is the substantial pre-formation of the fiber sample 18 into a plug 18 that has the general shape of the micronaire chamber 28.

Figure 2:
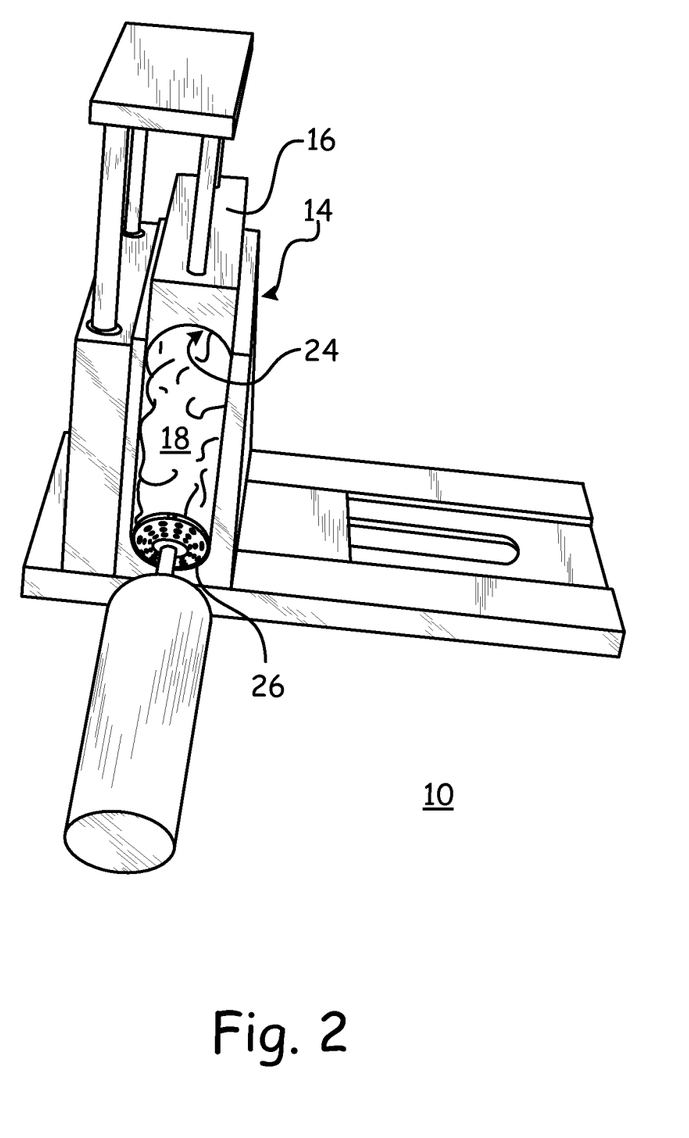
FIG. 2 depicts a micronaire measurement system according to a preferred embodiment of the present invention, with the loader in the lateral plug 18 formation position.

As depicted in the FIG. 2, and according to the configuration of the present example, the exterior lateral wall 22 of the loader 12 is brought toward the interior lateral wall 20 of the loader 12, thus laterally forming the fiber sample 18 into the shape of the micronaire chamber 28. More specifically, the bottom portion of the fiber sample 18 is formed into the shape of the micronaire chamber 28, by the two rounded bottom corners of the interior lateral wall 20 and the exterior lateral wall 22 that have been brought together.

As depicted in FIG. 2, the top formation member 24 preferably also has elements that assist in forming the fiber sample 18 into the shape of the micronaire chamber 28. In the example depicted, the top formation member 24 has a rounded interior surface, to approximate the interior of the micronaire chamber 28 at that equivalent location.

Figure 3:
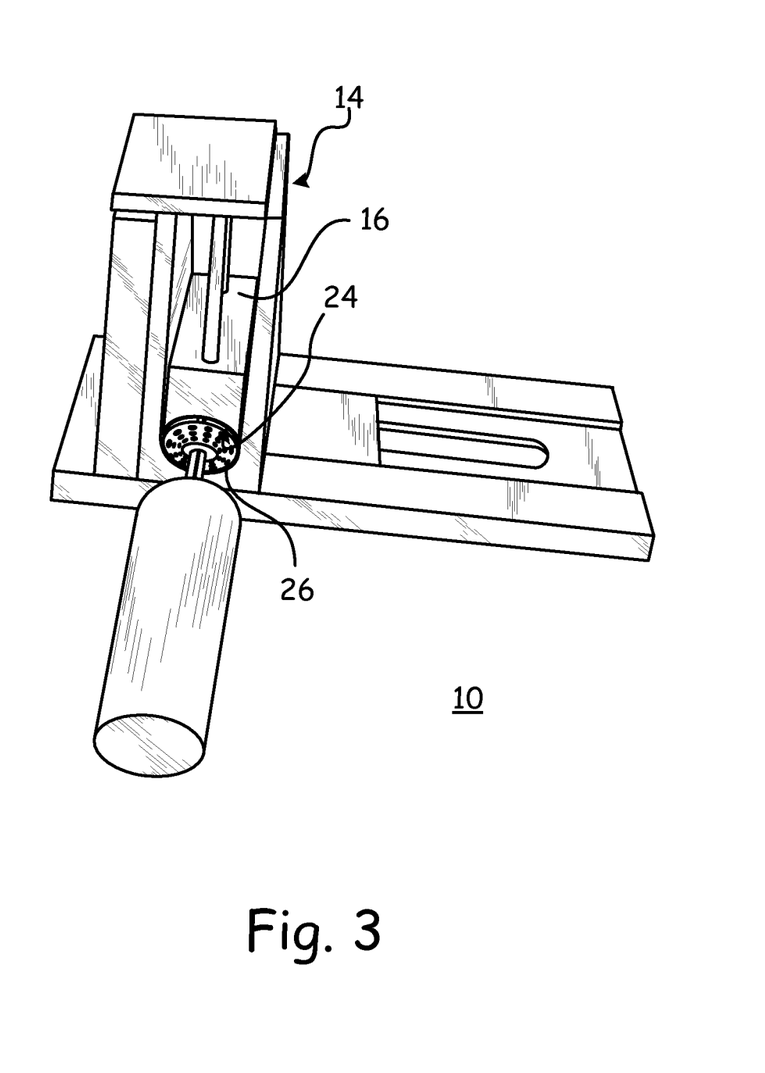
FIG. 3 depicts a micronaire measurement system according to a preferred embodiment of the present invention, with the loader in the vertical plug 18 formation position.

As depicted in FIG. 3, the top formation member 24 is brought down onto the fiber sample 18, to complete the formation of the fiber sample 18 into the shape of the micronaire chamber 28. It is appreciated that the order of the compaction by which the fiber sample 18 is formed into a plug 18 with the same cross-sectional shape as the micronaire chamber 28 is by way of example only, and that in various embodiments the plug 18 can be vertically shaped first and then laterally shaped, or the shaping members can be oriented into a configuration that is something other than orthogonal. All such configurations are within the contemplated scope of the present invention.

Also depicted in FIG. 3 is the forward plunger 26, which preferably also is configured to have a cross-sectional shape that is substantially equivalent to the cross-sectional shape of the micronaire chamber 28. As depicted in FIG. 3, the forward plunger 26 is preferably perforated, for purposes as described in more detail hereafter.

Figure 4:
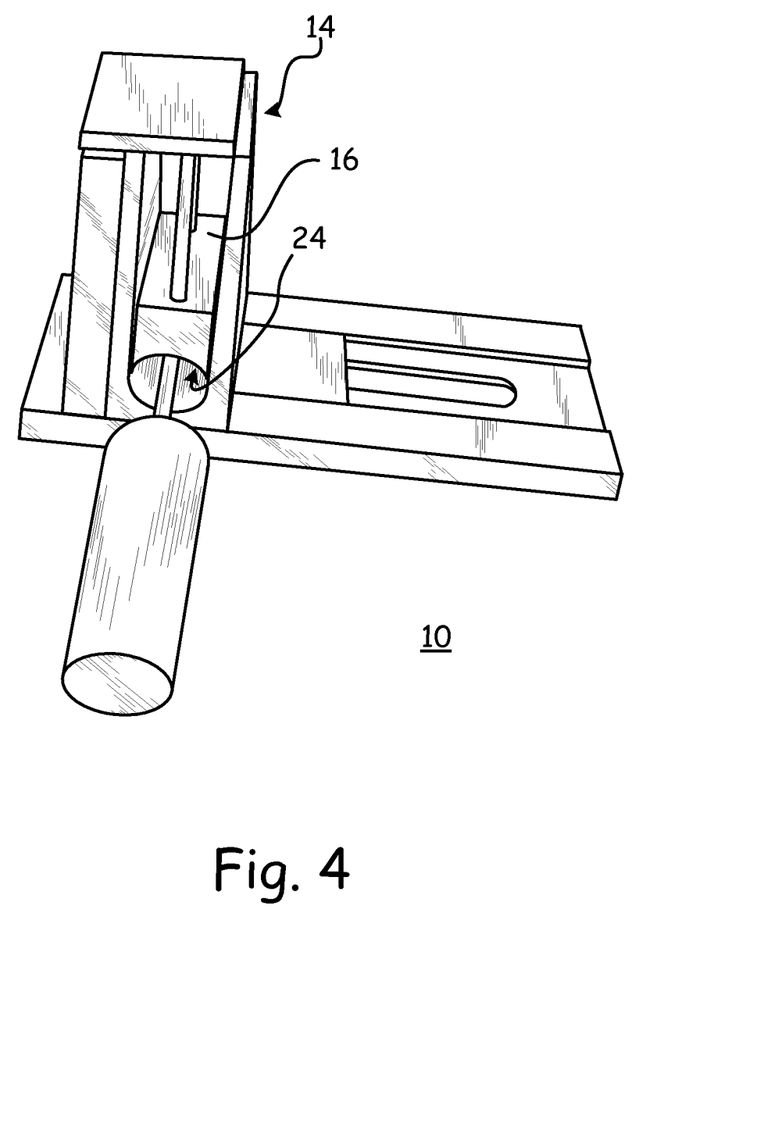
FIG. 4 depicts a micronaire measurement system according to a preferred embodiment of the present invention, with the loader in the plug 18 insertion position.

FIG. 4 depicts the loader 12 where the forward plunger 26 has been extended, thus driving the fiber sample 18, which has been formed by the loader into substantially the shape of the micronaire chamber 28, from the loader 12 and into the micronaire chamber 28. In alternate embodiments, however, the loader 12, after being configured to compact the fiber sample 18, then becomes the micronaire chamber 28, and no separate micronaire chamber 28 is required. In such an embodiment, the various moving elements of the loader 12 are preferably fashioned from materials that form substantially air-tight seals at the interfaces between them, or are fitted with edge moldings of such material.

Figure 5:
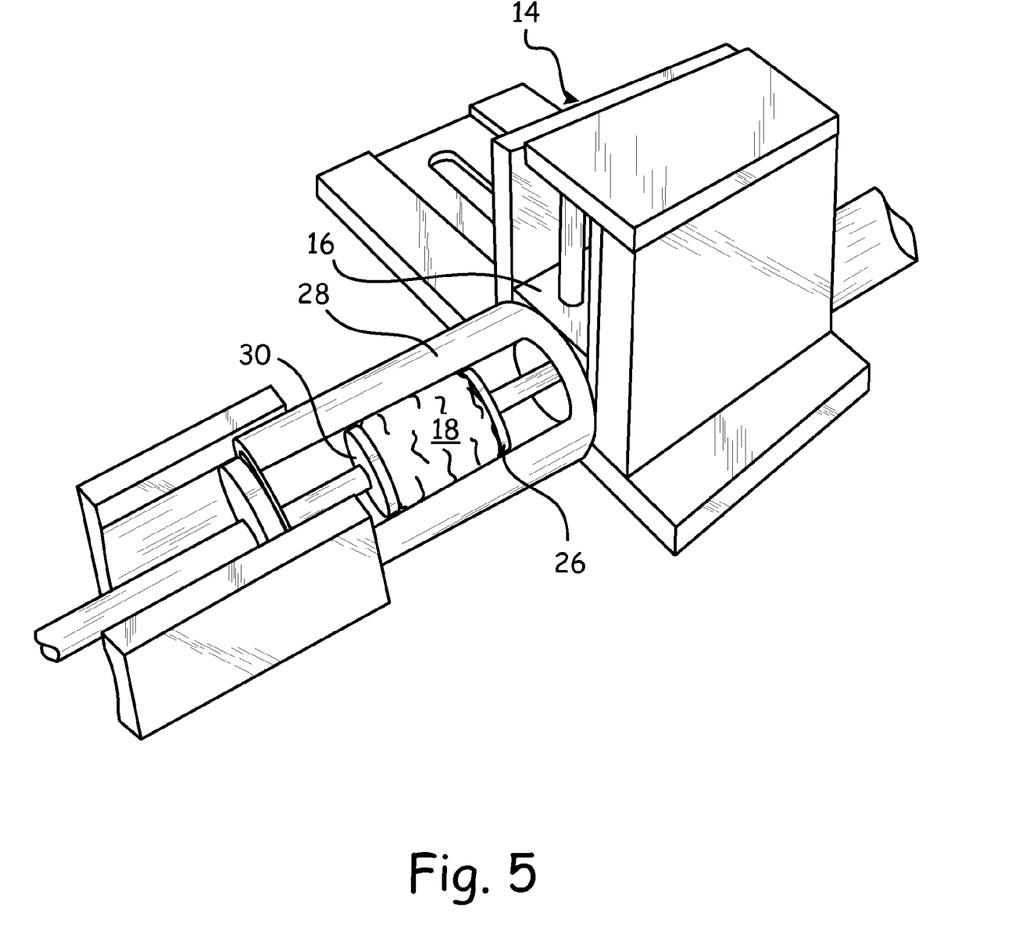
FIG. 5 depicts a micronaire measurement system according to a preferred embodiment of the present invention, with the plug 18 in the micronaire chamber 28.

As depicted in FIG. 5, in those embodiments where there is a separate micronaire chamber 28 into which the forward plunger 26 drives the fiber sample that has been pre-formed into a plug 18, the plug 18 meets the rear plunger 30 at the back of the micronaire chamber 28, and begins to be compacted in its length between the forward plunger 26 and the rear plunger 30 as the forward plunger 26 moves forward. In alternate embodiments, the forward plunger 26 can be brought to a point in the micronaire chamber 28 where the plug 18 has not yet compacted, and then the rear plunger 30 can be moved to compact the plug 18 against the forward plunger 26. Various other embodiments are also within the scope of this disclosure, such as where both plungers 26 and 30 move toward each other, or move in the same direct at differing speeds that produce a compaction of the fibers in the plug 18.

The methods by which the apparatus 10 takes the micronaire measurements are described in more detail hereafter. After the micronaire measurements have been taken on the plug 18, the plug 18 is preferably expelled from the apparatus 10. This can be accomplished be either withdrawing one of the forward plunger 26 and the rear plunger 30, and using the other plunger to expel the plug 18 from one or both of the micronaire chamber 28 or the loader 12. Alternately, and especially in those embodiments where the loader 12 comprises the micronaire chamber 28, the combined loader 12—micronaire chamber 28 can be opened up and the plug 18 can be withdrawn, either by gravity or some other means.

Figure 6:
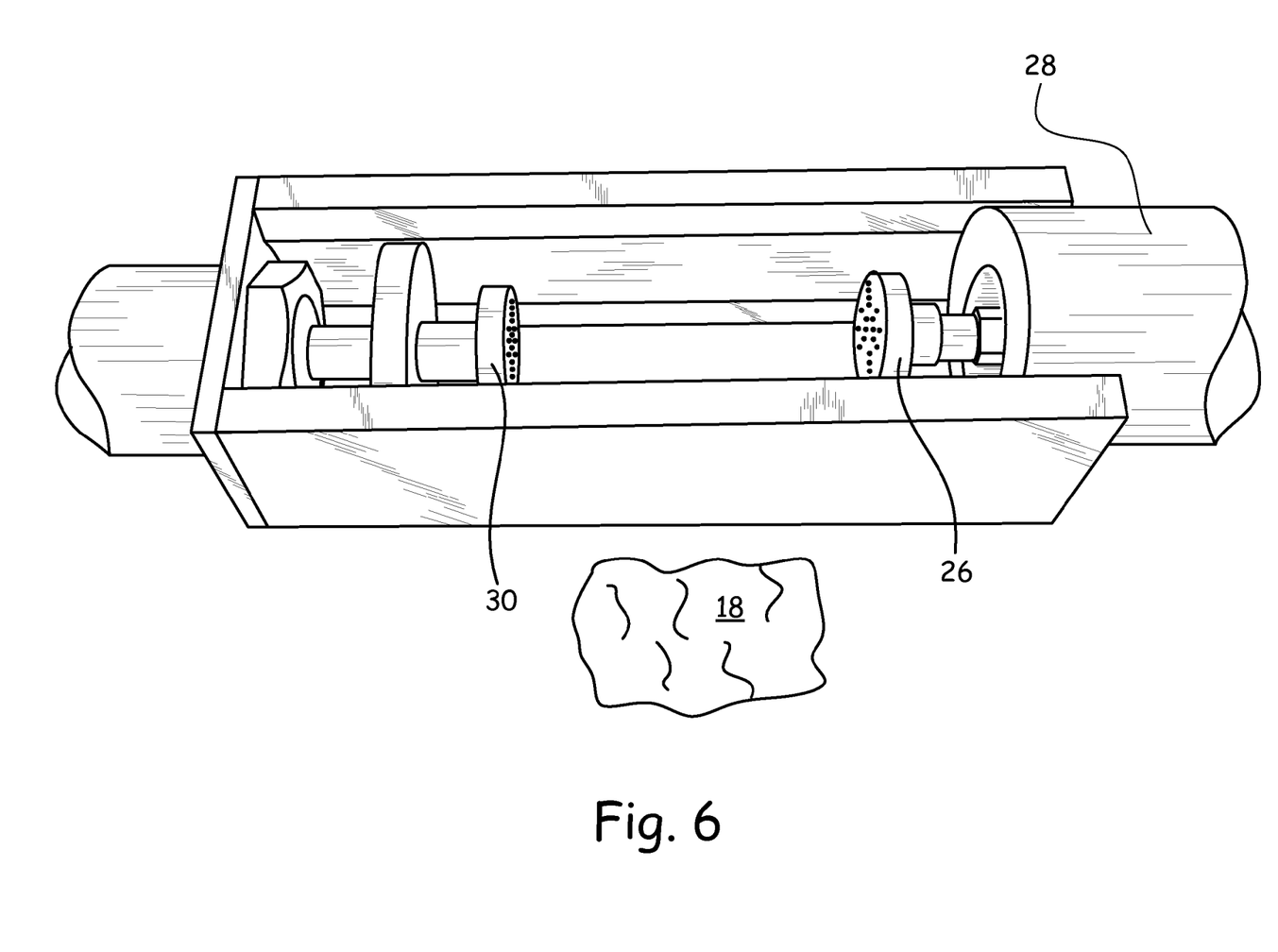
FIG. 6 depicts a micronaire measurement system according to a preferred embodiment of the present invention, with the loader in the plug 18 expulsion position.

FIG. 6 depicts an embodiment where the rear plunger 30 is withdrawn from the back of the bore of the micronaire chamber 28, and the forward plunger 26 pushes the plug 18 out the back of the bore of the micronaire chamber 28. The plug 18, similar to that as described in alternate embodiments above, can either fall from the micronaire chamber 28 or be withdrawn by some other removal means, such as a mechanical device or a vacuum-induced air flow.

In the preferred embodiment, the fiber sample 18 is weighed as a part of the micronaire measurement. Although the weight of the sample can be approximated in a variety of different ways, it has been determined that actually weighing the fiber sample 18 tends to produce more accurate micronaire readings. Weighing the fiber sample 18 can be accomplished either before or after the fiber sample 18 is formed into a plug 18 by the loader 12, and either before or after the plug 18 is processed in the micronaire chamber 28.

If the weight of the fiber sample 18 is not measured until after the micronaire measurements are taken in the micronaire chamber 28, such as after the plug 18 has been expelled from the micronaire chamber 28, then an actual micronaire reading might not be presented until after the fiber sample 18 has been weighed. Alternately, various means can be used to estimate the weight of the fiber sample 18, and those estimates can be used to provide a calculated micronaire reading for the fiber sample 18. Further yet, an estimated weight can be used for a preliminary calculation, which is then fine-tuned by the use of the actual weight of the fiber sample 18 after it has been weighed.

Micronaire Measurement

Figure 7:
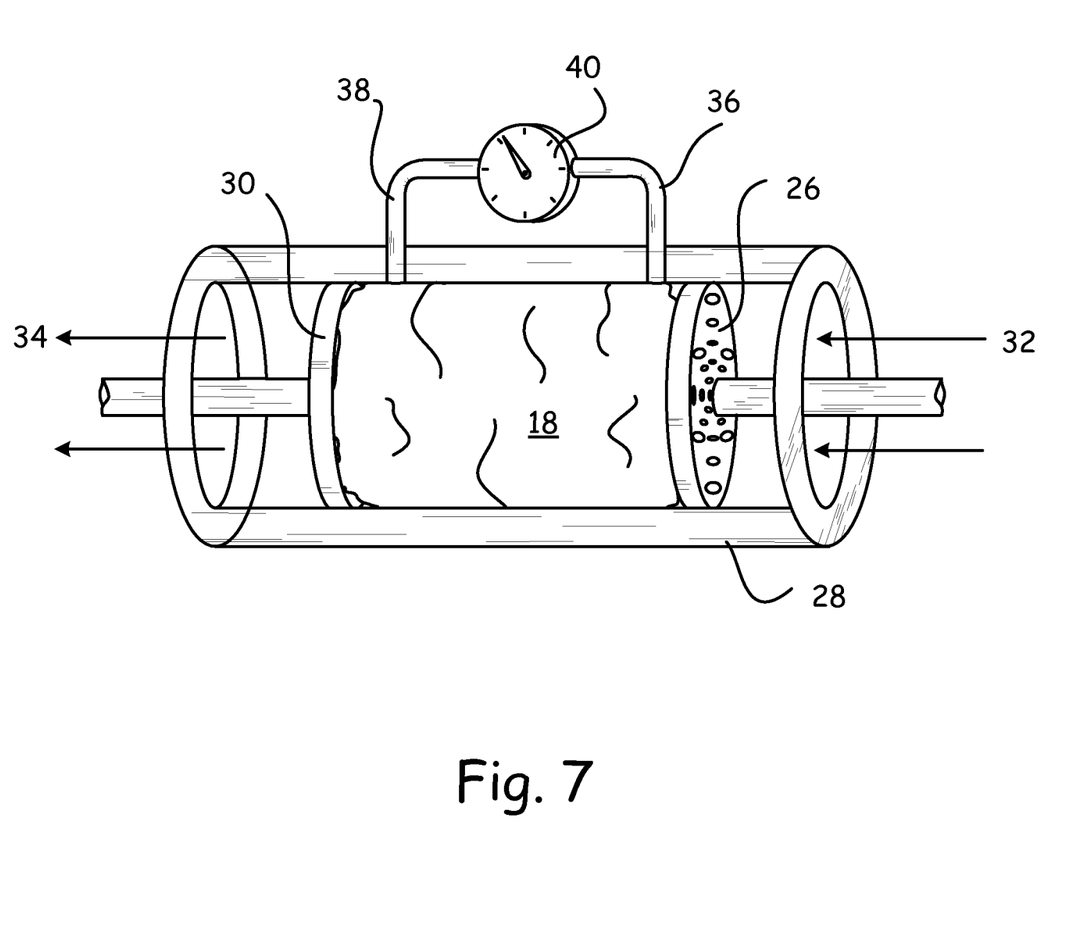
FIG. 7 is a functional block diagram of a micronaire measurement system according to a preferred embodiment of the present invention.

The apparatus 10 described above can be used in a variety of different ways to take micronaire readings. FIG. 7 depicts a functional block diagram of portions of the apparatus 10, which will be used to describe the micronaire measurements. In taking micronaire measurements, several parameters are preferably known, including the weight of the fiber sample 18, the volume of the portion of the micronaire chamber 28 in which the tests are conducted, the volumetric rate of the air flow that enters 32 and exits 34 the micronaire chamber 28, and the pressure differential within the micronaire chamber 28 as measured on a pressure differential meter 40 between an upstream pressure port 36 and a downstream pressure port 38. Information such as this is used in the equations as given above to calculate the micronaire of the fiber sample 18.

Preferably, the fiber sample 18 is compacted within the micronaire chamber 28 to a relatively consistent degree between the forward plunger 26 and the rear plunger 30, for all micronaire readings. Thus, if the fiber sample 18 has been weighed prior to testing, the volume of the micronaire chamber 28 can be set by bringing the forward plunger 26 and the rear plunger 30 relatively toward each other to form a volume that is based on the weight of the fiber sample 18 and an assumed density of the fiber sample 18.

If the fiber sample 18 has not been weighed prior to taking the readings, or if the weight of the fiber sample 18 is otherwise not to be used to determine the desired degree of compaction, then the desired degree of compaction can be set by turning on the air flow 32, and reducing the distance between the forward plunger 26 and the rear plunger 30 in a controlled manner, preferably such as at a constant velocity. This can be accomplished with stepper motors that drive one or both of the forward plunger 26 and the rear plunger 30. Various elements of the air flow properties of the air flow 32 are then monitored, which measured properties are then used to determine the desired micronaire chamber 28 length. Properties of the air flow 32 such as the volumetric flow and the pressure of the air flow 32/34 are generally referred to as air flow properties.

For example, the volumetric flow of the air flow 32 as delivered at a constant inlet pressure can be measured, and when the flow rate falls to a desired value, then the relative movement of the plungers 26 and 30 is stopped. Alternately, the air flow 32 is initiated, and as the degree of compaction increases the air flow resistance through the compacting fiber sample 18, the air flow decreases and the pressure increases. Either the reduction in the air flow or the increase in the pressure can be measured, and the plunger movement can be stopped when a desired set point is attained. In yet another alternate embodiment, a constant volumetric flow of the air flow 32 can be initiated, while the pressure required to produce the constant volumetric flow is measured. When the pressure required to produce the constant volumetric flow rises to a determined level, then the relative movement of the plungers 26 and 30 is stopped.

These air flow properties as monitored provide an indication of the degree of resistance to the air flow 32/34 through the compacted fiber sample 18, which in turn provides an indication of the degree of compaction of the fiber sample 18. At this point the distance between the plungers 26 and 30 is determined, so that the volume of the micronaire chamber 28 is known. The distance between the plungers 26 and 30 can be directly measured, sensed along the length of the micronaire chamber 28, or determined by tracking the progress of the stepper motors that drive one or both of the plungers 26 and 30.

The volume of the micronaire chamber 28 when a desired degree of compaction of the fiber sample 18 has been attained can also be used to estimate the weight of the fiber sample 18 within the micronaire chamber 28. In some embodiments this estimated weight of the fiber sample 18 is sufficient. However, if more accurate micronaire values are desired, then the fiber sample 18 is preferably weighed at some point before, during, or after the measurement process.

The micronaire chamber 28 preferably has an operable length of up to about six inches in which micronaire testing can be performed on a compacted fiber sample 18, so as to accommodate a wide range of fiber sample 18 weights. In this manner, the means by which the loader 12 is loaded with the fiber sample 18 does not need to be too sensitive in regard to the amount of the fiber sample 18 that is so loaded. Preferably the diameter of the bore of the micronaire chamber 28 is selected so that the length specified above can hold between about one and about ten grams of a cotton fiber sample 18.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of preparing a fiber sample for a micronaire measurement, the method comprising the step of forming the fiber sample into a plug having a cross-sectional shape and size that are substantially similar to a cross-sectional shape and size of a micronaire chamber in which the micronaire measurement is to be taken, before inserting the plug into the micronaire chamber.

2. A method of preparing a fiber sample for a micronaire measurement, the method comprising the steps of:
   placing an amount of unformed fiber as a fiber sample in a fiber sample loader, and
   bringing together forming surfaces of the fiber sample loader to form the fiber sample into an elongate plug having a cross-sectional shape and size that are substantially similar to a cross-sectional shape and size of a micronaire chamber in which the micronaire measurement is to be taken, before inserting the plug into the micronaire chamber.

3. A method of preparing a fiber sample for a micronaire measurement, the method comprising the steps of:
   placing an amount of unformed fiber as a fiber sample in a fiber sample loader, bringing a first lateral forming surface of the fiber sample loader toward a second lateral forming surface of the fiber sample loader and forming the fiber sample between the first lateral forming surface and the second lateral forming surface to form three sides of the fiber sample, bringing a vertical forming surface of the fiber sample loader down between the first lateral forming surface and the second lateral forming surface and onto the fiber sample to form a fourth side of the fiber sample, thereby forming the fiber sample into an elongate plug having a cross-sectional shape and size that are substantially similar to a cross-sectional shape and size of a micronaire chamber in which the micronaire measurement is to be taken, and inserting the plug into the micronaire chamber with a plunger having a cross-sectional shape and size that are substantially similar to the cross-sectional shape and size of a micronaire chamber in which the micronaire measurement is to be taken.

* * * * *